United States Patent
Dasgupta et al.

(10) Patent No.: US 10,653,597 B2
(45) Date of Patent: May 19, 2020

(54) ANTIMICROBIAL COMPOSITION COMPRISING THYMOL, TERPINEOL AND A CATIONIC PHOSPHOLIPID

(71) Applicant: Conopco, Inc., Englewood Cliffs, NJ (US)

(72) Inventors: Anindya Dasgupta, Bangalore (IN); Qiong Gu, Shanghai (CN); Kevin David Hermanson, Hamden, CT (US); Teanoosh Moaddel, Watertown, CT (US); Neha Salgaonkar, Bangalore (IN); Bo Shen, Shanghai (CN); Qiang Qiu, Easton, CT (US)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

(21) Appl. No.: 16/092,554

(22) PCT Filed: Mar. 30, 2017

(86) PCT No.: PCT/EP2017/057610
§ 371 (c)(1),
(2) Date: Oct. 10, 2018

(87) PCT Pub. No.: WO2017/178240
PCT Pub. Date: Oct. 19, 2017

(65) Prior Publication Data
US 2019/0117538 A1 Apr. 25, 2019

(30) Foreign Application Priority Data
Apr. 14, 2016 (WO) ............... PCT/CN2016/079293
Jun. 27, 2016 (EP) ..................... 16176486

(51) Int. Cl.
*A61K 8/34* (2006.01)
*A61K 8/55* (2006.01)
*A61Q 17/00* (2006.01)
*A61Q 19/10* (2006.01)
*A01N 33/12* (2006.01)
*A01N 31/04* (2006.01)
*A61K 31/045* (2006.01)
*A61K 31/685* (2006.01)
*C11D 1/62* (2006.01)
*A01N 31/08* (2006.01)
*C11D 3/20* (2006.01)
*A61K 31/05* (2006.01)
*C11D 3/48* (2006.01)
*A01N 57/12* (2006.01)
*A61K 8/37* (2006.01)
*A61K 8/67* (2006.01)
*A61K 8/891* (2006.01)

(52) U.S. Cl.
CPC .............. *A61K 8/347* (2013.01); *A01N 31/04* (2013.01); *A01N 31/08* (2013.01); *A01N 33/12* (2013.01); *A01N 57/12* (2013.01); *A61K 8/34* (2013.01); *A61K 8/553* (2013.01); *A61K 31/045* (2013.01); *A61K 31/05* (2013.01); *A61K 31/685* (2013.01); *A61Q 17/005* (2013.01); *A61Q 19/10* (2013.01); *C11D 1/62* (2013.01); *C11D 3/2034* (2013.01); *C11D 3/2037* (2013.01); *C11D 3/48* (2013.01); *A61K 8/37* (2013.01); *A61K 8/675* (2013.01); *A61K 8/891* (2013.01); *A61K 2800/5922* (2013.01); *A61K 2800/74* (2013.01)

(58) Field of Classification Search
CPC ........ A61K 8/347; A61K 31/045; A61K 8/34; A61K 8/553; A61K 31/05; A61K 31/685; A61K 8/891; A61K 8/675; A61K 2800/74; A61K 8/37; A61K 2800/5922; A01N 57/12; A01N 31/04; A01N 31/08; A01N 33/12; C11D 3/2037; C11D 3/2034; C11D 1/62; C11D 3/48; A61Q 17/005; A61Q 19/10
See application file for complete search history.

(56) References Cited

U.S. PATENT DOCUMENTS

| | | | |
|---|---|---|---|
| 5,208,257 A * | 5/1993 | Kabara | A01N 37/12 514/552 |
| 2004/0014818 A1 | 1/2004 | Boeck et al. | |
| 2005/0101515 A1 | 5/2005 | Pawson et al. | |
| 2014/0045692 A1 | 2/2014 | Rossines et al. | |
| 2014/0364509 A1 * | 12/2014 | Wegner | A61K 8/34 514/724 |
| 2015/0306007 A1 | 10/2015 | Golas et al. | |

FOREIGN PATENT DOCUMENTS

| | | | | |
|---|---|---|---|---|
| EP | 2348838 | | 8/2011 | |
| EP | 16176486 .5 | * | 6/2016 | ........... A61K 31/685 |

(Continued)

OTHER PUBLICATIONS

Ning et al. (CN104688810 (A) English translation) (Year: 2015).*
IPRP2 in PCTEP2017057610.
Manuel Viuda-Martos et al.; Chemical Composition of the Essential Oils Obtained From Some Spices Widely Used in Mediterranean Region; Acta Chim. Slov. ; 2007; pp. 921-926, XP055302524; vol. 54.
Anti Acne leave-on expert clearing gel; Mintel GNPD; 2016; pp. 1-3, XP002761835 (Mintel Record ID: 4091587).

(Continued)

*Primary Examiner* — Aradhana Sasan
*Assistant Examiner* — Quanglong N Truong
(74) *Attorney, Agent, or Firm* — Krista A. Kostiew

(57) ABSTRACT

The present invention relates to an antimicrobial composition and more particularly an antimicrobial composition for leave-on applications. The present invention discloses an antimicrobial composition comprising; a) 0.01 to 2% by weight of thymol; b) 0.01 to 2% by weight of terpineol; and c) 0.1 to 2% by weight of a cationic phospholipid complex.

11 Claims, No Drawings

(56) References Cited

FOREIGN PATENT DOCUMENTS

GB            508407      6/1939
WO    WO2010046238    4/2010

OTHER PUBLICATIONS

Search Report and Written Opinion in PCTEP2017057610; dated Jun. 22, 2017.
Search Report & Written Opinion in EP16176486; dated Sep. 28, 2016.
Written Opinion 2 in PCTEP2017057610; dated Mar. 9, 2018.

* cited by examiner

ANTIMICROBIAL COMPOSITION COMPRISING THYMOL, TERPINEOL AND A CATIONIC PHOSPHOLIPID

TECHNICAL FIELD

The present invention relates to an antimicrobial composition and more particularly an antimicrobial composition for leave-on applications.

BACKGROUND OF THE INVENTION

People try to take good care of the external surface of their bodies. Specific skin related issues that people care about include good skin health free of infections, good skin tone and skin hygiene. Skin hygiene is generally achieved by keeping them free of infections. One way to tackle infections is to treat them with antimicrobials after the infection has set in. Another approach is to leave a minimal amount of antimicrobial active on the surface so that any invading microorganism is killed or inactivated to minimize spread of diseases. Yet another approach is improving the innate immunity of the desired surface.

The greatness of leave-on formulation is that it remains on the skin after the application. Therefore, one can deliver enhanced antimicrobial activity through leave-on formulations.

There are different antimicrobial compositions known in the art:

WO 2010/046238 (Unilever) discloses an antimicrobial composition for cleansing or personal care. It is an object of the present invention to provide antimicrobial compositions that have relatively fast antimicrobial action. Present inventors have surprisingly found that compositions comprising selected ingredients, namely thymol and terpineol, in selective propositions provide relatively quick antimicrobial action.

US 2004/0014818 (Boeck) discloses a bactericidal preparation in the form of a solution, cream or ointment compounded from photosynthesized hydrocarbons, isolates from hydrocarbons, 2-hydroxy-1-isopropyl-4-methyl benzene (thymol) and butylated hydroxytoluene and exemplifies many compositions, each having from 10 to 20 compounds having anti-bacterial efficacy.

GB508407 (Shepherd, 1938) describes an antiseptic product and method of preparation thereof comprising the steps of mixing salol and thymol in weight ratio of 1:3, melting the mixture and cooling to form crystals. An example of composition comprising 59 parts of the crystals, 41 parts of terpineol, 200 parts of red turkey oil and 200 parts of water is described. The composition described in this document comprises about 8% by weight thymol and about 8% by weight terpineol and is said to be particularly useful for disinfection of air.

Though the prior art discloses compositions for antimicrobial benefits, still there is a need to provide an antimicrobial leave-on composition which can have antimicrobial efficacy for long time with minimal amount of known antimicrobial ingredients.

It is therefore an object of the present invention to provide an antimicrobial composition.

It is another object of the present invention to provide an antimicrobial composition for leave-on application.

It is yet another object of the present invention to provide an antimicrobial composition for leave-on application, which has prolonged antimicrobial activity.

It is yet a further object of the present invention to provide an antimicrobial composition for leave-on application that employs minimal amount of known antimicrobial compounds.

The present inventors while working extensively on this have surprisingly found that a composition with a little amount of thymol, terpineol and a cationic phospholipid complex provides an antimicrobial composition with good and prolonged antimicrobial activity which cannot be achieved by using little amount of only thymol and terpineol thereby satisfying one or more of the above mentioned objects.

SUMMARY OF THE INVENTION

In a first aspect, the present invention provides an antimicrobial composition comprising;
a) 0.01 to 2% by weight of thymol;
b) 0.01 to 2% by weight of terpineol; and
c) 0.1 to 2% by weight of a cationic phospholipid complex.

In a second aspect, the present invention provides a method of disinfecting a surface comprising the steps of applying a composition of the first aspect on to said surface.

In a third aspect, the present invention provides use of a cationic phospholipid complex in an antimicrobial composition comprising thymol and terpineol to increase the antimicrobial activity.

Any feature of one aspect of the present invention may be utilized in any other aspect of the invention. The word "comprising" is intended to mean "including" but not necessarily "consisting of" or "composed of." In other words, the listed steps or options need not be exhaustive. Except in the operating and comparative examples, or where otherwise explicitly indicated, all numbers in this description indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

DETAILED DESCRIPTION OF THE INVENTION

The present invention provides an antimicrobial composition comprising;
a) 0.01 to 2% by weight of thymol;
b) 0.01 to 2% by weight of terpineol; and
c) 0.1 to 2% by weight of a cationic phospholipid complex.

Antimicrobial composition as mentioned herein above preferably means any composition which is capable of killing or at least cause substantial reduction of the common disease causing microbes. The common disease causing gram-positive organisms includes *Staphylococcus, Streptococcus* and *Enterococcus* spp. Some of common disease causing gram-negative organisms includes *Escherichia coli, Salmonella, Klebsiella* and *Shigella*. *Escherichia coli* and *Salmonella* can cause severe gastrointestinal illnesses.

The composition of the present invention is preferably in the form of a leave-on composition. Leave-on composition preferably means compositions that are applied on a surface (e.g. skin) without a subsequent step of washing the surface to effect the removal of the composition after the application. This preferably means the compositions stays on the surface after the application.

Thymol:

The antimicrobial composition of the present invention comprises thymol. The amount of thymol preferably is in the range of 0.01 to 2%, more preferably 0.01 to 1% and further more preferably 0.01 to 0.5%, most preferably 0.01 to 0.1% and further most preferably 0.01 to 0.05%. The composition of the present invention are able to provide the required antimicrobial benefit at very low concentration of thymol. At concentrations higher than the higher preferred concentrations of thymol, when in combination with terpineol, while the kinetics of action would not be compromised, the present inventors have found that unlike in therapeutic/pesticidal/herbicidal applications where sensorial aspects are not critical, in the present application, which is preferably a personal care applications, the product is in contact with hands or other body parts, the sensorial aspects like smell and skin feel would be compromised. Thymol may be added to the antimicrobial composition in purified form.

The amount of thymol used in the composition of the present invention is preferably very low. The present inventors have found that at the low concentration of thymol when combine with the other essential ingredients of the composition able to provide good and prolonged/long-lasting antimicrobial action.

Alternatively, thyme oil or thyme extract comprising thymol may be added to the antimicrobial composition, while ensuring that thymol is present in the desired concentration in the composition of the present invention. Thyme oil or thyme extract is obtained from the thyme plant. Thyme plant refers to a plant belonging be genus *Thymus* and includes but is not limited to the following species: *Thymus vulgaris, Thymus zygis, Thymus satureoides, Thymus mastichina, Thymus broussonetti, Thymus maroccanus, Thymus pallidus, Thymus algeriensis, Thymus serpyllum, Thymus pulegoide,* and *Thymus citriodorus*. The isomer of thymol (carvacrol) may also preferably be used.

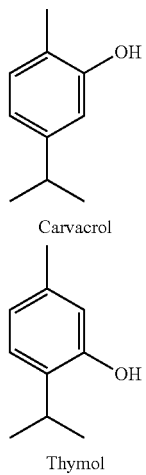

Carvacrol

Thymol

Terpineol:

The antimicrobial composition of the present invention also comprises terpineol. The amount of terpineol preferably is in the range of 0.01 to 2%, more preferably 0.01 to 1% and further more preferably 0.01 to 0.5%, most preferably 0.01 to 0.1% and further most preferably 0.01 to 0.05%. The composition of the present invention are able to provide the required antimicrobial benefit at very low concentration of terpineol. At concentrations higher than the higher preferred concentrations of terpineol, when in combination with thymol, while the kinetics of action would not be compromised, the present inventors have found that unlike in therapeutic/pesticidal/herbicidal applications where sensorial aspects are not critical, in the present application, which is preferably a personal care applications, the product is in contact with hands or other body parts, the sensorial aspects like smell and skin feel would be compromised. Terpineol may be added to the antimicrobial composition in purified form.

The amount of terpineol used in the composition of the present invention is preferably very low. The present inventors have found that at the low concentration of terpineol when combine with the other essential ingredients of the composition able to provide prolonged/long-lasting antimicrobial action.

The structure of a terpineol is given below:

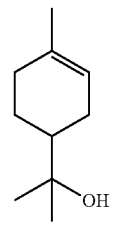

Alternatively, pine oil comprising terpineol may be added to the antimicrobial composition.

Cationic Phospholipid Complex:

The antimicrobial composition of the present invention also comprises a cationic phospholipid complex, also known as a cationic phospholipid compound.

Phospholipids are a class of lipids that are major constituents of all cell membranes. They are having amphiphilic characteristics; hence, they can form lipid bilayers. The structure of the phospholipid molecule generally consists of two hydrophobic fatty acid "tails" and a hydrophilic "head".

The preferred cationic phospholipid complex of the composition of the present invention comprises diester phosphatides.

Linoleamidopropyl PG-Dimonium Chloride Phosphate is the most preferred cationic phospholipid complex for the composition of the present invention. It has the following structure:

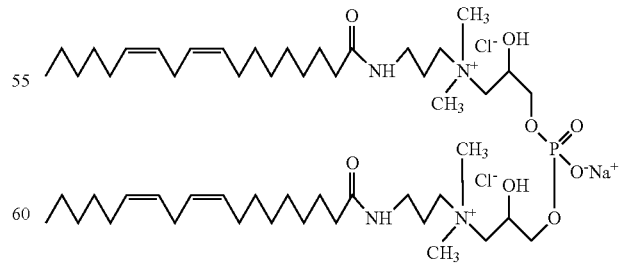

Linoleamidopropyl PG-Dimonium Chloride Phosphate composed of multiple chains of predominantly diester phosphatides. It is derived from safflower oil containing a high level of linoleic acid.

The amount of phospholipid complex is in the range of 0.1 to 2%, preferably 0.1 to 1% and most preferably 0.1 to 0.5% by weight of the composition.

The composition of the present invention also preferably comprises an oil blend.

The term 'oil blend' preferably means additional oil mix, other than thymol and terpineol, which is used for providing enhanced sensorials to the personal care leave-on formulation.

Oil generally provides good sensorial properties for a leave-on type composition. It is preferred to have oil in a leave-on type composition. The composition of the present invention preferably comprises 3 to 30%, more preferably 5 to 30%, further more preferably 10 to 30% and most preferably 20 to 30% by weight of an oil blend.

The oil blend preferably comprises saturated triglycerides and linear dimethicone.

Dimethicones with different viscosity may preferably be added together to optimize the rheological property of the composition.

It is preferred that the saturated triglycerides comprises a mixture of Capric and Caprylic triglyceride. In a most preferred scenario, the ratio of Capric to Caprylic in the saturated triglyceride is in the range of 60:40 to 80:20 and most preferably is 70:30.

We have found that the addition of little amount of oil blend affects the performance of the antimicrobial activity of the composition of the present invention. However, with the increasing amount of the oil blend the antimicrobial activity regains.

The composition of the present invention preferably comprises a cosmetically acceptable base.

The cosmetically acceptable base is preferably a cream, lotion, gel or emulsion.

Personal care compositions (leave-on) may be prepared using different cosmetically acceptable emulsifying or non-emulsifying systems and vehicles. A highly suitable base is a cream. Vanishing creams are especially preferred. Vanishing cream bases generally comprise 5 to 25% fatty acid and 0.1 to 10% soap. Vanishing cream base gives a highly appreciated matty feel to the skin. C12 to C20 fatty acids are especially preferred in vanishing cream bases, further more preferred being C14 to C18 fatty acids. The most preferred fatty acid is stearic acid. The fatty acid in the composition is more preferably present in an amount in the range of 5 to 20% by weight of the composition. Soaps in the vanishing cream base include alkali metal salt of fatty acids, like sodium or potassium salts, most preferred being potassium stearate. The soap in the vanishing cream base is generally present in an amount in the range of 0.1 to 10%, more preferably 0.1 to 3% by weight of the composition. Generally, the vanishing cream base in personal care compositions is prepared by taking a desired amount of total fatty matter and mixing with potassium hydroxide in desired amounts. The soap is usually formed insitu during the mixing.

An especially suitable cosmetically acceptable base is one which comprises a water-in-oil emulsion comprising silicone oils as the continuous phase. The water in oil emulsions preferably comprise a cross-linked silicone elastomer blend.

Inclusion of silicone elastomer blend in a water-in-oil emulsion may be used as the cosmetically acceptable base for preparing the compositions of the present invention. While silicone fluids may be used, silicone elastomers which are cross-linked, are especially preferred. In contrast to silicone fluid polymers, the physical properties of elastomers are typically dependent on the number of cross-linkages, rather than molecular weight. The ability of silicone elastomers to swell makes them ideal thickeners for oil phases. The elastomers have a very smooth and soft feel when applied to skin or hair. They can also be used as delivery agents for fragrances, vitamins and other additives in cosmetic compositions.

Suitable silicone elastomer blends or gels which are commercially available and suitable for inclusion in the composition of the invention and found to provide the enhanced stability are: Dow Corning® EL-8051 IN Silicone Organic Elastomer Blend [INCI Name: Isodecyl Neopentanoate (and) Dimethicone/Bis Isobutyl PPG-20 Crosspolymer]; EL-8050 [INCI Name: Isododecane (and) Dimethicone/Bis-Isobutyl PPG 20 Crosspolymer] DC 9040, DC9041, DC9045 (Dimethicone crosspolymer); DC 9506, 9509 (Dimethicone vinyl dimethicone crosspolymer); Shin-Etsu KSG-15, KSG-16, KSG-17 (Dimethicone vinyl dimethicone crosspolymer). It is further preferred that the composition comprises 5 to 50% silicone elastomer by weight of the composition.

The composition of the invention preferably comprises 0.1 to 5% by weight of Niacinamide or its derivatives thereof. Any derivatives of niacinamide that are having similar property to niacinamide may preferably be used. Apart from niacinamide, other well known skin lightening agents e.g. aloe extract, ammonium lactate, arbutin, azelaic acid, kojic acid, butyl hydroxy anisole, butyl hydroxy toluene, citrate esters, 3 diphenyl propane derivatives, 2, 5 dihydroxybenzoic acid and its derivatives, ellagic acid, fennel extract, gluco pyranosyl-1-ascorbate, gluconic acid, glycolic acid, green tea extract, hydroquinone, 4 hydroxyanisole and its derivatives, 4-hydroxy benzoic acid derivatives, hydroxycaprylic acid, lemon extract, linoleic acid, magnesium ascorbyl phosphate, mulberry root extract, 2,4 resorcinol derivatives, 3,5 resorcinol derivatives, salicylic acid, vitamins like vitamin B6, vitamin B12, vitamin C, vitamin A, a dicarboxylic acid, resorcinol derivatives, hydroxycarboxylic acid like lactic acid and their salts e.g. sodium lactate, and mixtures thereof.

Additionally, though not preferred, the composition may have sunscreen. Any sunscreen that can be suitably used with the base may be added. Both, UVA and UVB sunscreens may preferably be added.

The composition of the invention may preferably comprises a UV-A sunscreen which is a dibenzoylmethane or its derivatives. Preferred dibenzoylmethane derivatives are selected from 4-tert-butyl-4'-methoxydibenzoylmethane, 2-methyldibenzoylmethane, 4-methyldibenzoylmethane, 4-isopropyldibenzoyl-methane, 4-tert-butyldibenzoylmethane, 2,4-dimethyldibenzoylmethane, 2,5-dimethyldibenzoylmethane, 4,4'-diisopropyl-dibenzoylmethane, 2-methyl-5-isopropyl-4'-methoxydibenzoylmethane, 2-methyl-5-tert-butyl-4'-methoxy-dibenzoyl methane, 2,4-dimethyl-4'-methoxy dibenzoylmethane or 2,6-dimethyl-4-tert-butyl-4'-methoxy-dibenzoylmethane. The most preferred dibenzoylmethane derivative is 4-tert.-butyl-4'-methoxy-dibenzoylmethane. The composition of the invention preferably comprises 0.1 to 10%, more preferably 0.2 to 5%, further more preferably 0.4 to 3%, by weight dibenzoylmethane or a derivative thereof based on total weight of the composition and including all ranges subsumed therein.

The composition may also preferably comprises a UV-B organic sunscreen selected from the class of cinnamic acid, salicylic acid, diphenyl acrylic acid and derivatives thereof. Illustrative non-limiting example of UV-B sunscreens which are commercially available and useful for inclusion in the composition of the invention are Octisalate™, Homosalate™, NeoHelipan™, Octocrylene™, Oxybenzone™ or Parsol MCX™. The UV-B sunscreen is most preferably 2-ethyl-hexyl-4-methoxy cinnamate which is commercially available as Parsol MCX. The UV-B organic sunscreen is preferably included in 0.1 to 10%, more preferably 0.1 to 7% by weight of the composition. It has been observed that presence of an organic UV-B sunscreen like 2-ethyl-hexyl-4-methoxy cinnamate causes further rapid degradation of the UV-A dibenzoylmethane sunscreen in the presence of UV radiation. The presence of the rosmarinic acid ester compound is found to be very efficacious in stabilizing the composition even when UV-B sunscreens are present.

Useful inorganic sun-blocks are also preferably used in the present invention. These include, for example, zinc oxide, iron oxide, silica, such as fumed silica, and titanium dioxide.

Preservatives can also be added into the compositions to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Particularly preferred preservatives are phenoxyethanol, methyl paraben, propyl paraben, imidazolidinyl urea, sodium dehydroacetate, benzyl alcohol, alkane diols most preferably 1,2-octane diol and phenoxyethanol. The preservatives should be selected having regard for the use of the composition and possible incompatibility between the preservatives and other ingredients. Preservatives are preferably employed in amounts ranging from 0.01% to 2% by weight of the composition.

A variety of other optional materials may be formulated into the compositions. These may include: antimicrobials such as 2-hydroxy-4,2',4'-trichlorodiphenylether (triclosan), 2,6-dimethyl-4-hydroxychlorobenzene, and 3,4,4'-trichlorocarbanilide; scrub and exfoliating particles such as polyethylene and silica or alumina; cooling agents such as menthol; skin calming agents such as aloe vera; and colorants.

In addition, the compositions may further include 0 to 10% by weight of opacifiers and pearlizers such as ethylene glycol distearate, titanium dioxide or Lytron® 621 (Styrene/Acrylate copolymer); all of which are useful in enhancing the appearance or properties of the product.

Diluents other than water can include liquid or solid emollients, solvents, humectants, thickeners and powders. Examples of each of these types of vehicle, which can be used singly or as mixtures of one or more vehicles, are as follows:

Emollients, such as stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rape seed oil, safflower seed oil, evening primrose oil, soybean oil, sunflower seed oil, avocado oil, sesame seed oil, coconut oil, *arachis* oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate;

Solvents, such as ethyl alcohol, isopropanol, acetone, ethylene glycol monoethyl ether, diethylene glycol monobutyl ether, diethylene glycol monoethyl ether; Advantageously, active agents other than skin conditioning agents defined above may be added to the composition. These active ingredients may be advantageously selected from bactericides, vitamins, anti-acne actives; anti-wrinkle, anti-skin atrophy and skin repair actives; skin barrier repair actives; non-steroidal cosmetic soothing actives; artificial tanning agents and accelerators; skin lightening actives; sunscreen actives; sebum stimulators; sebum inhibitors; anti-oxidants; protease inhibitors; skin tightening agents; anti-itch ingredients; hair growth inhibitors; 5-alpha reductase inhibitors; desquamating enzyme enhancers; anti-glycation agents; or mixtures thereof; and the like.

These active agents may be selected from water-soluble active agents, oil soluble active agents, pharmaceutically acceptable salts and mixtures thereof. The term "active agent" as used herein, means personal care actives which can be used to deliver a benefit to the skin and/or hair and which generally are not used to confer a skin conditioning benefit, such are delivered by emollients as defined above. The term "safe and effective amount" as used herein, means an amount of active agent high enough to modify the condition to be treated or to deliver the desired skin care benefit, but low enough to avoid serious side effects. The term "benefit," as used herein, means the therapeutic, prophylactic, and/or chronic benefits associated with treating a particular condition with one or more of the active agents described herein. What is a safe and effective amount of the active agent(s) will vary with the specific active agent, the ability of the active to penetrate through the skin, the age, health condition, and skin condition of the user, and other like factors.

Powders, such as chalk, talc, fullers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The cosmetically acceptable base is usually from 10 to 99.9%, preferably from 50 to 99% by weight of the composition, and can, in the absence of other personal care adjuncts, form the balance of the composition.

The composition of the invention may preferably comprises a conventional deodorant base as the cosmetically acceptable carrier. By a deodorant is meant a product in the stick, roll-on, or propellant medium which is used for personal deodorant benefit e.g. application in the under-arm area which may or may not contain anti-perspirant actives.

Deodorant compositions can generally be in the form of firm solids, soft solids, gels, creams, and liquids and are dispensed using applicators appropriate to the physical characteristics of the composition. Deodorant compositions which are delivered through roll-ons generally comprise a liquid carrier. Such liquid carrier can be hydrophobic or comprise a mixture of both hydrophilic and hydrophobic liquids. They may be in the form of an emulsion or a microemulsion. The liquid carrier or mixture of carriers often constitutes from 30 to 95% by weight of the composition and in many instances from 40 to 80%. Hydrophobic liquid carriers commonly can comprise one or more materials selected within the chemical classes of siloxanes, hydrocarbons, branched aliphatic alcohols, esters and ethers that have a melting point not higher than 25° C. and a boiling point of at least 100° C. Hydrophilic carrier liquids that can be employed in compositions herein commonly comprise water and/or a mono or polyhydric alcohol or water-miscible homologue. Monohydric alcohols often are short chain, by which is meant that they contain up to 6 carbons, and in practice is most often ethanol or sometimes iso-propanol. Polyhydric alcohols commonly comprise ethylene or propylene glycol, or a homologue can be employed such as diethylene glycol. Other than this suitable other vehicle and component used for deodorant composition can be added.

When the composition is in the form of a hand sanitizer composition the cosmetically acceptable base may comprises of alcohol and water. The most preferred alcohols are ethyl alcohol and isopropyl alcohol. Even a mixture of two or more alcohol can preferably be used in the hand sanitizer composition. The amount of alcohol preferably in the range of 50 to 95%, more preferably 60 to 80% and most preferably 65 to 80% by weight of the hand sanitizer composition.

The compositions of the present invention can comprise a wide range of other optional components. The CTFA Personal care Ingredient Handbook, Second Edition, 1992, which is incorporated by reference herein in its entirety, describes a wide variety of non-limiting personal care and pharmaceutical ingredients commonly used in the skin care industry, which are suitable for use in the compositions of the present invention. Examples include: antioxidants, binders, biological additives, buffering agents, colorants, thickeners, polymers, astringents, fragrance, humectants, opacifying agents, conditioners, pH adjusters, natural extracts, essential oils, skin sensates, skin soothing agents, and skin healing agents.

The composition of the present invention may also comprises one or more of the following ingredients e.g. benzethonium chloride (BEC), benzalkonium chloride (BKC), chloroxylenol, zinc pyrithione (ZPT), creatine and creatinine.

The present invention also discloses a method of disinfecting a surface comprising the steps of applying a composition according to the invention on to said surface.

The present invention also discloses a use of a composition of the present invention as disclosed above for improved antimicrobial benefit. Improved antimicrobial benefit preferably means after application of the composition of the present invention the residual microbes on the surface is significantly less. Therefore the composition of the present invention able to provide prolonged/long-lasting antimicrobial benefits. The preferred intended use of the composition of the present invention is non-therapeutic and/or cosmetic.

The present invention also relates to use of a cationic phospholipid complex in an antimicrobial composition comprising thymol and terpineol to increase the antimicrobial activity. Preferably, the cationic phospholipid complex, the thymol and the terpineol are present in synergistic amounts, that is, in amounts capable of synergistically providing the antimicrobial activity. Preferably, the use relates to use in a composition comprising 0.01 to 2% by weight of thymol and 0.01 to 2% by weight of terpineol. For use according to the present invention, the cationic phospholipid complex is preferably present in an amount of 0.1 to 2% by weight. Here, all percentages are by weight of the total composition. The cationic phospholipid complex preferably comprises diester phosphatides. More preferably, the cationic phospholipid complex is Linoleamidopropyl PG-Dimonium Chloride Phosphate. Preferences regarding the antimicrobial composition according to the first aspect and the cationic phospholipid complex comprised therein as described hereinbefore apply equally to the use of a phospholipid complex in an antimicrobial composition according to the third aspect of the invention.

Now the invention will be demonstrated by the following non-limiting example.

EXAMPLES

To check the efficacy different leave-on formulations were prepared as follows:

Example A

For this example, the base formulation was prepared according to the following Table 1.

TABLE 1

| Ingredient | Wt % |
|---|---|
| Glycerin | 3 |
| 1,3-Butylene glycol | 2 |
| Stearic acid | 0.1 |
| Disodium EDTA | 0.1 |
| Methacrylate copolymer | 0.25 |
| Ethanol | 3 |
| Ammonium Acryloyldimethyltaurate | 1.2 |
| Water | To 100 |

For this purpose 1,3-Butylene glycol was procured from Calanese®, Methacrylate copolymer and Ammonium Acryloyldimethyltaurate was procured from Clariant®.

Example B

To the base formulation of Example 1, 0.1% of a mixture of thymol and terpineol (0.05% thymol and 0.05% terpineol) was added. The additional amount was adjusted by the water amount.

Example 1

In this example, additionally 0.5% of Linoleamidopropyl PG-Dimonium Chloride Phosphate (obtained from Croda under the trade name Arlasilk PFA) was added in the formulation of Example B. The additional amount was adjusted by the water amount.

Example 2

In this example, further 6.75% of an oil blend was added to the formulation of Example 1. For this purpose, the oil blend was prepared by mixing 6.25% of linear dimethicone of different viscosity (6% of DC200-10 cst from Dow Corning and 0.25% of DC200-50 cst From Dow Corning) and 0.5% of capric/caprylic triglycerides (from Croda under trade name GTCC). The additional amount was adjusted by the amount of water.

Example 3

This example is same as Example 2 except 13.5% oil blend has been used instead of 6.75. For this purpose, the oil blend was prepared by mixing 12.5% of linear dimethicone of different viscosity (12% of DC200-10 cst and 0.5% of DC200-50 cst) and 1% of capric/caprylic triglycerides (GTCC). The additional amount was adjusted by the amount of water.

Example 4

This example is also same as Example 2 except 27% oil blend has been used instead of 6.75. For this purpose, the oil blend was prepared by mixing 25% of linear dimethicone of different viscosity (24% of DC200-10 cst and 1% of DC200-50 cst) and 2% of capric/caprylic triglycerides (GTCC). The additional amount was adjusted by the amount of water.

Invitro Time-Kill Test with the Leave-on Formulations

Test Bacteria: *S. Epidermidis* ATCC 12228

Test Conditions:

The formulations as prepared above were added as it is without any dilution.

The temperature of the experiment was 35±2° C.

The time of contact tested for 1 hour and 2 hour.

Bacteria Culture Preparation:

The test organisms were no more than five passages removed from the original source. The stock culture as obtained was transferred to a growth media and left it for 24 hours at 35±2° C. in a shaker incubator. The growth media used was Tryptic Soy Broth from Difco®. A glycerol stock of the said culture was prepared by adding the culture in 50% glycerol in 1:1 ratio by volume. From the glycerol stocks, the test organism was streaked on a TSA slant (Tryptic Soy Agar, Difco®). Then the slant was incubated at 35±2° C. for about 24 hours. The culture was then streaked on a TSA plate and incubated again at 35° C.±2 for about 18 hours. After that, the plate culture was gently scraped and re-suspended in sterile saline sufficient to achieve a minimum final suspension of 1×10$^8$ CFU/mL (OD at 620 nm).

Test Procedure:

For each formulation 10 g of sample was taken and about 2.5×10$^7$ of the test bacteria (as prepared above) were added and vortexed thoroughly for 30 seconds. After that, these samples were then incubated at about 37° C. in an incubator (Bacteriological Incubator, Labtop®) and samples were collected for further testing after 1 hour and 2 hour. Post incubation (i.e. after 1 hour or 2 hour respectively), 1 g of the test sample was weighted and added to 9 ml D/E diluent (D/E neutralizer, Difco®) and vortexed for around 30 seconds and left as it is for about 5 minutes. A serial ten-fold dilutions of the neutralized samples were prepared by taking 1 mL of neutralized samples and using 9.0 mL dilution media (D/E neutralizer, Difco®). 1 mL of each diluted sample was plated in duplicate on a TSA plate and incubated at 35±2° C. for 48 hours.

As a standard procedure, for this Test a culture control sample was taken which was only with bacteria (without any formulations).

After 48 hours the bacterial colonies were counted and multiplied by the dilution factor to calculate CFU/mL. The counts were converted to log 10 values and the Log reduction was calculated accordingly by subtracting the initial value from the test value.

The results of these experiments are summarized below in Table 2.

TABLE 2

| Example No | Log reduction | |
|---|---|---|
| | 1 hour | 2 hour |
| A | 0.1 ± 0.15 | 0.09 ± 0.12 |
| B | 0.03 ± 0.17 | 0.02 ± 0.13 |
| 1 | 1.0 ± 0.29 | 3.78 ± 0.83 |
| 2 | 0.45 ± 0.1 | 2.57 ± 0.46 |
| 3 | 0.63 ± 0.14 | 2.91 ± 0.74 |
| 4 | 0.8 ± 0.12 | 3.2 ± 0.44 |

From the above table it is evident that the compositions that are within the scope of the present invention (Example 1 to 4) provides significantly better microbial protection when compared to compositions that are outside the scope of the present invention (Example A and B). It is also clear that with the addition of little amount of oil blend (Example 2) the antimicrobial effect is bit reduced (compared to Example 1). However, with increasing amount of oil blend (example 4) it regains the efficacy. Nevertheless though the efficacy of Example 2 is little less than that of Example 1, however it is still much better than that of control examples (Example A and B).

The invention claimed is:

1. An antimicrobial composition comprising;
   a) 0.01 to 2% by weight of thymol;
   b) 0.01 to 2% by weight of terpineol; and
   c) 0.1 to 2% by weight of a cationic phospholipid complex wherein the cationic phospholipid complex is linoleamidopropyl PG-dimonium chloride phosphate.

2. The composition of claim 1 wherein the amount of thymol is in the range of 0.01 to 0.5% by weight.

3. The composition of claim 1 wherein the amount of terpineol is in the range of 0.01 to 0.5% by weight.

4. The composition of claim 1 comprises 3 to 30% by weight of an oil blend.

5. The composition of claim 4 wherein the oil blend comprises saturated triglycerides and linear dimethicone.

6. The composition of claim 5 wherein the saturated triglycerides comprises a mixture of capric and caprylic triglyceride.

7. The composition of claim 6 wherein the ratio of capric to caprylic is in the range of 60:40 to 80:20.

8. The composition of claim 1 further comprising a cosmetically acceptable base.

9. The composition of claim 1 further comprising 0.1 to 5% by weight of niacinamide or its derivatives thereof.

10. The composition of claim 1 in the form of a leave-on composition.

11. A method of cleaning or disinfecting a surface comprising the steps of applying a composition of claim 1 on to said surface.

* * * * *